United States Patent
Ishizuka et al.

(10) Patent No.: US 9,844,494 B2
(45) Date of Patent: Dec. 19, 2017

(54) TWO-PASTE POLYMERIZABLE COMPOSTION

(71) Applicant: GC CORPORATION, Tokyo (JP)

(72) Inventors: So Ishizuka, Tokyo (JP); Naofumi Matsumoto, Tokyo (JP)

(73) Assignee: GC CORPORATION, Tokyo (JP)

( * ) Notice: Subject to any disclaimer, the term of this patent is extended or adjusted under 35 U.S.C. 154(b) by 0 days.

(21) Appl. No.: 15/124,495

(22) PCT Filed: Mar. 6, 2015

(86) PCT No.: PCT/JP2015/056734
§ 371 (c)(1),
(2) Date: Sep. 8, 2016

(87) PCT Pub. No.: WO2015/146550
PCT Pub. Date: Oct. 1, 2015

(65) Prior Publication Data
US 2017/0014311 A1    Jan. 19, 2017

(30) Foreign Application Priority Data

Mar. 24, 2014  (JP) ................................ 2014-060873

(51) Int. Cl.
| | | |
|---|---|---|
| A61K 6/00 | (2006.01) |
| A61K 6/083 | (2006.01) |
| A61K 6/10 | (2006.01) |
| C08L 33/10 | (2006.01) |
| C08F 220/68 | (2006.01) |

(52) U.S. Cl.
CPC .............. *A61K 6/005* (2013.01); *A61K 6/083* (2013.01); *A61K 6/10* (2013.01); *C08F 220/68* (2013.01)

(58) Field of Classification Search
None
See application file for complete search history.

(56) References Cited

U.S. PATENT DOCUMENTS

| | | | | |
|---|---|---|---|---|
| 5,043,361 A * | 8/1991 | Kubota | .................. | A61K 6/083 522/10 |
| 5,883,153 A * | 3/1999 | Roberts | ................ | A61K 6/0017 501/151 |
| 6,214,101 B1 * | 4/2001 | Nakaseko | ............ | A61K 6/0017 106/35 |
| 6,288,138 B1 * | 9/2001 | Yamamoto | ........... | A61K 6/0023 522/17 |
| 2004/0068041 A1 * | 4/2004 | Nakayama | ................. | C08J 3/24 524/493 |
| 2007/0031779 A1 * | 2/2007 | Tokui | ....................... | A61C 5/62 433/89 |
| 2007/0040151 A1 * | 2/2007 | Utterodt | ............... | A61K 6/0017 252/182.13 |
| 2007/0100019 A1 * | 5/2007 | Sun | ...................... | A61K 6/0017 523/116 |
| 2010/0311864 A1 * | 12/2010 | Arita | ..................... | A61K 6/0029 523/118 |
| 2013/0274426 A1 * | 10/2013 | Sugiura | .................. | A61K 6/083 526/123.1 |
| 2016/0213577 A1 * | 7/2016 | Matsumoto | .......... | A61K 6/0017 |

FOREIGN PATENT DOCUMENTS

| | | |
|---|---|---|
| JP | 62-246514 A | 10/1987 |
| JP | 2003-105008 A | 4/2003 |
| JP | 2007-056020 A | 3/2007 |
| JP | 2008-088086 A | 4/2008 |
| JP | 2009-503086 A | 1/2009 |
| JP | 2011-016776 A | 1/2011 |
| JP | 2013-100242 A | 5/2013 |

OTHER PUBLICATIONS

International Search Report dated May 26, 2015; PCT/JP2015/056734.

* cited by examiner

*Primary Examiner* — Peter A Salamon
(74) *Attorney, Agent, or Firm* — Ladas & Parry LLP; Loren K. Thompson

(57) ABSTRACT

Provided is a polymerizable composition hardly having oxygen inhibition layer by polymerization under an oxygen environment, including a first paste including (a) a (meth)acrylate compound, (b) at least one of an aromatic sulfinic acid and a salt thereof, and (c) an acidic compound; and a second paste including (a) a (meth)acrylate compound, (d) an organic metal compound, and (e) an organic halogen compound, wherein at least either one of the first paste and the second paste includes (f) a filler.

5 Claims, No Drawings

TWO-PASTE POLYMERIZABLE COMPOSTION

TECHNICAL FIELD

The present invention relates to polymerizable compositions used in dental treatment, and more specifically relates to two-paste polymerizable compositions hardly having oxygen inhibition layers by polymerization under an oxygen environment.

BACKGROUND ART

Combinations of an organic peroxide and an aromatic tertiary amine have been used since a long time ago, as a polymerization initiator for polymerizing a paste composition containing radically-polymerizable methacrylate or acrylate monomers, oligomers thereof, and prepolymers thereof (for example, see Patent Literature 1). In the combinations, time for polymerization and curing is adjusted, and a preservation stability is given to the paste composition before polymerization, by adjusting the amounts of the organic peroxide and the aromatic tertiary amine to be blended in the paste composition, and using a polymerization inhibitor at the same time.

On the other hand, it is known that oxygen inhibition layers are generated in the composition by polymerization under an oxygen environment (polymerization inhibition), and there are problems, for example the composition has a bad operability as a dental polymerizable composition such as a composite resin for repairing, a resin for constructing tooth foundations, and a resin for producing temporary prostheses, and grinding is difficult to carry out thereto.

As a combination of polymerization initiators, disclosed is a paste type polymerizable composition including a ternary catalyst of a pyrimidinetrione derivative, an organic metal compound, and an organic halogen compound (for example see Patent Literature 2). However, this composition also has a problem of polymerization inhibition.

Further, a dental composition in which hydroperoxide, a thiourea derivative, and a copper compound are combined (for example, see Patent Literature 3), a dental composition including a hydrogen peroxide-polyvinylpyrrolidone complex (for example, see Patent Literature 4), a composition including cumene hydroperoxide and acetylthiourea (for example, see Patent Literature 5), and the like are disclosed. However, even with these dental compositions, the problem of polymerization inhibition has not been solved.

Another disclosure is a redox curing type dental composition including a first agent and a second agent, wherein both the first and second agents contain a polymerizable monomer, and either one of the first and second agents contains an oxidation agent, and the other one of the first and second agents contains a reducing agent, at least one of an aromatic sulfinic acid and a salt thereof, and a ternary aliphatic amine (for example, see Patent Literature 6). However, even with this composition, the problem of polymerization inhibition has not been solved.

As a method for reducing the polymerization inhibition, disclosed is a technique of adding a layered silicate mineral for inhibiting the generation of oxygen inhibition layers (for example, see Patent Literature 7). However, unnecessary addition of mineral has a problem of causing the operability and polymerization property to get worse and causing the strength of the hardened body to degrade.

CITATION LIST

Patent Literatures

Patent Literature 1: JP S62-246514 A
Patent Literature 2: JP 2003-105008 A
Patent Literature 3: JP 2007-056020 A
Patent Literature 4: JP 2008-088086 A
Patent Literature 5: JP 2009-503086 T
Patent Literature 6: JP 2011-016776 A
Patent Literature 7: JP 2013-100242 A

SUMMARY OF INVENTION

Technical Problem

An object of the present invention is to provide a polymerizable composition hardly having oxygen inhibition layers by polymerization under an oxygen environment

Solution to Problem

As a result of intensive researches, the inventors of the present invention found that a polymerizable composition in which a polymerization initiator formed from a combination of at least either one of an aromatic sulfinic acid and a salt thereof; an organic metal compound, and an organic halogen compound is blended can keep a high catalyst activity even in polymerization under an oxygen environment, and it is possible to obtain a hardened body having little oxygen inhibition layers. The present invention has been completed based on the above findings.

That is, a first embodiment of the present invention is a two-paste polymerizable composition including:
 a first paste including
  (a) a (meth)acrylate compound,
  (b) at least one of an aromatic sulfinic acid and a salt thereof, and
  (c) an acidic compound; and
 a second paste including
  (a) a (meth)acrylate compound,
  (d) an organic metal compound, and
  (e) an organic halogen compound,
wherein at least either one of the first paste and the second paste includes (f) a filler.

A second embodiment of the present invention is a two-paste polymerizable composition
including:
 a first paste including
 (a') a (meth)acrylate compound not having acid groups,
 (a") a (meth)acrylate compound having an acid group(s), and
 (b) at least one of an aromatic sulfinic acid and a salt thereof; and
 a second paste including
 (a) a (meth)acrylate compound,
 (d) an organic metal compound, and
 (e) an organic halogen compound,
wherein at least either one of the first paste and the second paste includes (f) a filler.

A third embodiment of the present invention is a two-paste polymerizable composition
including:
 a first paste including
 (a) a (meth)acrylate compound,
 (b) at least one of an aromatic sulfinic acid and a salt thereof, and
 (c) an acidic compound; and a second paste including
(a) a (meth)acrylate compound,
(d) an organic metal compound, and
(e) an organic halogen compound,
wherein neither the first paste nor the second paste includes (f) a filler.

Advantageous Effects of Invention

The two-paste polymerizable composition according to the present invention is a good polymerizable composition hardly having oxygen inhibition layers by polymerization under an oxygen environment.

DESCRIPTION OF EMBODIMENTS

Hereinafter the two-paste polymerizable composition according to the present invention will be described in detail.

In the present invention, the first and second embodiments will be together described. One paste in the two-paste polymerizable composition according to the present invention will be referred to as a first paste.

In the first embodiment of the present invention, the first paste includes (a) a (meth)acrylate compound, (b) at least one of an aromatic sulfinic acid and a salt thereof, and (c) an acidic compound. The first paste may further include (f) a filler in the relationship with the second paste which is described later.

In the second embodiment of the present invention, the first paste includes (a') a (meth)acrylate compound not having acid groups, (a") a (meth)acrylate compound having an acid group(s), and (b) at least one of an aromatic sulfinic acid and a salt thereof. The first paste may further include (f) a filler in the relationship with the second paste which is described later.

That is, the second embodiment of the present invention is the same as the first embodiment except that the second embodiment includes both (a') a (meth)acrylate compound not having acid groups and (a") a (meth)acrylate compound having an acid group(s), as (a) a (meth)acrylate compound, and (c) an acid compound in the first embodiment is not an essential component. Therefore there are no distinctions between the explanations of the first and second embodiments, except the above-mentioned differences.

A (meth)acrylate compound which is the component (a) is to be a base material of the polymerizable composition by polymerization and curing. In the present invention, "(meth) acrylate compound" includes monomers, oligomers and prepolymers of various kinds of acrylate compounds or methacrylate compounds.

(a) a (meth)acrylate compound may further be divided into (a') a (meth)acrylate compound not having acid groups and (a") a (meth)acrylate compound having an acid group(s).

Here, in the second embodiment of the present invention, the first paste certainly includes (a") a (meth)acrylate compound having an acid group(s). Therefore the first paste does not necessarily include (c) an acidic compound.

Specific examples of (a') a (meth)acrylate compound not having acid groups include methyl(meth)acrylate, ethyl (meth)acrylate, isopropyl(meth)acrylate, n-butyl(meth)acrylate, isobutyl(meth)acrylate, hydroxypropyl(meth)acrylate, tetrahydrofurfuryl(meth)acrylate, glycidyl(meth)acrylate, 2-hydroxyethyl(meth)acrylate, 3-hydroxypropyl(meth)acrylate, 2-methoxyethyl(meth)acrylate, 2-ethoxyethyl(meth) acrylate, 2-ethylhexyl(meth)acrylate, benzil(meth)acrylate, 2-hydroxy-1,3-di(meth)acryloxypropane, ethyleneglycoldi (meth)acrylate, diethyleneglycoldi(meth)acrylate, triethyleneglycoldi(meth)acrylate, butyleneglycoldi(meth)acrylate, neopentylglycoldi(meth)acrylate, 1,3-butanedioldi(meth) acrylate, 1,4-butanedioldi(meth)acrylate, 1,6-hexanedioldi (meth)acrylate, trimethylolpropanetri(meth)acrylate, trimethylolethanetri(meth)acrylate, pentaerythritoltri(meth) acrylate, trimethylolmethanetri(meth)acrylate, pentaerythritoltetra(meth)acrylate, polybutyleneglycoldi (meth)acrylate, and bisphenol A diglycidyl(meth)acrylate. Their monomers, oligomers, and prepolymers may be preferably used. As a (meth)acrylate having an urethane bond(s), di-2-(meth)acryloxyethyl-2,2,4-trimethylhexamethylenedicarbamate, 1,3,5-tris[1,3-bis{(meth)acryloyloxy}-2-propoxycarbonylaminohexane]-1,3,5-(1H,3H,5H)tri azine-2,4,6-trione, 2,2-bis[4-{3-(meth)acryloyloxy-2-hydroxypropyl}phenyl]propane, 2,2-bis[4-{(meth) acryloxyethoxy}phenyl]propane and the like may be given, and in addition, a (meth)acrylate of urethane oligomer formed from: 2,2'-di(4-hydroxycyclohexyl)propane; 2-oxypanone; hexamethylenediisocyanate; and 2-hydroxyethyl (meth)acrylate, a (meth)acrylate of urethane oligomer formed from: 1,3-butanediol; hexamethylenediisocyanate; and 2-hydroxyethyl(meth)acrylate, and the like may be given for example. They may be used alone, and a mixture of two or more kinds thereof may also be used.

Examples of (a") a (meth)acrylate compound having an acidic group(s) include (meth)acrylate compounds having at least one acid group, such as phosphoric acid group, pyrophosphoric acid group, thiophosphoric acid group, phosphonic acid group, sulfonic acid group, and carboxylic acid group.

In the examples of (a") a (meth)acrylate compound having an acid group(s), examples of a (meth)acylate compound having a phosphoric acid group(s) include 2-(meth)acryloyloxyethyldihydrogenphosphate,
3-(meth)acryloyloxypropyldihydrogenphosphate,
4-(meth)acryloyloxybutyldihydrogenphosphate,
5-(meth)acryloyloxypentyldihydrogenphosphate,
6-(meth)acryloyloxyhexyldihydrogenphosphate,
7-(meth)acryloyloxyheptyldihydrogenphosphate,
8-(meth)acryloyloxyoctyldihydrogenphosphate,
9-(meth)acryloyloxynonyldihydrogenphosphate,
10-(meth)acryloyloxydecyldihydrogenphosphate,
11-(meth)acryloyloxyundecyldihydrogenphosphate,
12-(meth)acryloyloxydodecyldihydrogenphosphate,
16-(meth)acryloyloxyhexadecyldihydrogenphosphate,
20-(meth)acryloyloxyicosyldihydrogenphosphate,
bis[2-(meth)acryloyloxyethyl]hydrogenphosphate,
bis[4-(meth)acryloyloxybutyl]hydrogenphosphate,
bis[6-(meth)acryloyloxyhexyl]hydrogenphosphate,
bis[8-(meth)acryloyloxyoctyl]hydrogenphosphate,
bis[9-(meth)acryloyloxynonyl]hydrogenphosphate,
bis[10-(meth)acryloyloxydecyl]hydrogenphosphate,
1,3-di(meth)acryloyloxypropyldihydrogenphosphate,
2-(meth)acryloyloxyethylphenylhydrogenphosphate,
2-(meth)acryloyloxyethyl-2-bromoethylhydrogenphosphate,
bis[2-(meth)acryloyloxy-(1-hydroxymethypethyl]hydrogenphosphate, acid chlorides thereof, alkali metal salts thereof, and ammonium salts thereof.

In examples of (a") a (meth)acrylate compound having an acidic acid group(s), examples of a (meth)acrylate compound having a pyrophosphoric acid group(s) include pyrophosphoric acid bis[2-(meth)acryloyloxyethyl], pyrophosphoric acid bis[4-(meth)acryloyloxybutyl], pyrophosphoric acid bis[6-(meth)acryloyloxyhexyl], pyrophosphoric acid bis[8-(meth)acryloyloxyoctyl], pyrophosphoric acid bis[10-(meth)acryloyloxydecyl], acid chlorides thereof, alkali metal salts thereof, and ammonium salts thereof.

In the examples of (a") a (meth)acrylate compound having an acid group(s), examples of a (meth)acrylate compound having a thiophosphoric acid group(s) include
  2-(meth)acryloyloxyethyldihydrogenthiophosphate,
  3-(meth)acryloyloxypropyldihydrogenthiophosphate,
  4-(meth)acryloyloxybutyldihydrogenthiophosphate,
  5-(meth)acryloyloxypentyldihydrogenthiophosphate,
  6-(m eth)acryloyloxyhexyldihydrogenthiophosphate,
  7-(meth)acryloyloxyheptyldihydrogenthiophosphate,
  8-(meth)acryloyloxyoctyldihydrogenthiophosphate,
  9-(meth)acryloyloxynonyldihydrogenthiophosphate,
  10-(meth)acryloyloxydecyldihydrogenthiophosphate,
  11-(meth)acryloyloxyundecyldihydrogenthiophosphate,
  12-(meth)acryloyloxydodecyldihydrogenthiophosphate,
  16-(meth)acryloyloxyhexadecyldihydrogenthiophosphate,
  20-(meth)acryloyloxyicosyldihydrogenthiophosphate,
acid chlorides thereof, alkali metal salts thereof, and ammonium salts thereof.

In the examples of (a") a (meth)acrylate compound having an acid group(s), examples of a (meth)acrylate compound having a phosphonic acid group(s) include
  2-(meth)acryloyloxyethylphenylphosphonate,
  5-(meth)acryloyloxypentyl-3-phosphonopropionate,
  6-(meth)acryloyloxyhexyl-3-phosphonopropionate,
  10-(meth)acryloyloxydecyl-3-phosphonopropionate,
  6-(meth)acryloyloxyhexyl-3-phosphonoacetate,
  10-(meth)acryloyloxydecyl-3-phosphonoacetate, acid chlorides thereof, alkali metal salts thereof, and ammonium salts thereof.

In the examples of (a") a (meth)acrylate compound having an acid group(s), examples of a (meth)acrylate compound having a sulfonic acid group(s) include 2-(meth)acrylamide-2-methylpropanesulfonic acid, and 2-sulfoethyl(meth)acrylate.

In the examples of (a") a (meth)acrylate compound having an acid group(s), examples of a (meth)acrylate compound having a carboxylic acid group(s) include a polymerizable monomer having one carboxyl group in the molecule, and a polymerizable monomer having a plurality of carboxyl groups in the molecule. As the polymerizable monomer having one carboxyl group in the molecule, (meth)acrylic acid, N-(meth)acryloylglycine, N-(meth)acryloylaspartic acid, N-(meth)acryloyl-5-aminosalicylic acid, O-(meth)acryloyltyrosine, N-(meth)acryloyltyrosine, N-(meth)acryloylphenylalanine, N-(meth)acryloyl-p-aminobeonzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, acid halides thereof and the like may be given for example.

In the examples of (a") a (meth)acrylate compound having an acid group(s), examples of a (meth)acrylate compound having a plurality of carboxyl groups in the molecule include 2-(meth)acryloyloxyethylhydrogensuccinate,
  2-(meth)acryloyloxyethylhydrogenphthalate, 2-(meth)acryloyloxyethylhydrogenmaleate,
  6-(meth)acryloyloxyhexane-1,1-dicarboxylic acid,
  9-(meth)acryloyloxynonane-1,1-dicarboxylic acid,
  10-(meth)acryloyloxydecane-1,1-dicarboxylic acid,
  11-(meth)acryloyloxyundecane-1,1-dicarboxylic acid,
  12-(meth)acryloyloxydodecane-1,1-dicarboxylic acid,
  13-(meth)acryloyloxytridecane-1,1-dicarboxylic acid,
  4-(meth)acryloyloxyethyltrimellitate,
  4-(meth)acryloyloxybutyltrimellitate, 4-(meth)acryloyloxyhexyltrimellitate,
  4-(meth)acryloyloxydecyltrimellitate,
  2-(meth)acryloyloxyethyl-3'-(meth)acryloyloxy-2'-(3,4-dicarboxybenzoyloxy)propylsuccinate, acid anhydrides thereof, and acid halides thereof.

The above-listed examples of (a') a (meth)acrylate compound not having acid groups and (a") a (meth)acrylate compound having an acid group(s) may be used alone, or a mixture of two or more kinds thereof may also be used.

In the first embodiment of the present invention, the blending amount of (a) a (meth)acrylate compound to the first paste is preferably in the range of from 15 mass % to 95 mass %. If the amount is less than 15 mass %, it is difficult to make a paste, if the amount is more than 95 mass %, the operability degrades and the strength also tends to degrade. More preferably, the amount is in the range of from 40 mass % to 80 mass %.

In the second embodiment of the present invention, the total blending amount of (a) a (meth)acrylate compound and (a") a (meth)acrylate compound having an acid group(s) to the first paste is preferably in the range of from 15 mass % to 95 mass %. If the amount is less than 15 mass %, it is difficult to make the paste, if the amount is more than 95 mass%, the operability degrades and the strength also tends to degrade. More preferably, the amount is in the range of from 40 mass % to 80 mass %.

At least one of an aromatic sulfinic acid and a salt thereof which is the component (b) reacts with (d) an organic metal compound and (e) an organic halogen compound, to generate radicals. By the polymerization initiator of this combination, it is possible to avoid oxygen inhibition layers of the composition in polymerization. Specific examples thereof include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-methylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. They may be used alone, and a mixture of two or more kinds thereof may also be used.

Among them, in view of preservation stability and polymerization activity, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate are especially preferable.

The blending amount of (b) at least one of an aromatic sulfinic acid and a salt thereof is preferably in the range of from 0.01 mass % to 5 mass %. If the amount is less than 0.01 mass %, a sufficient effect is difficult to be obtained, and even if the amount is more than 5 mass %, the effect is nearly unchanged. More preferably, the amount is in the range of from 0.1 mass % to 3 mass %.

In the first embodiment of the present invention, an acidic compound which is the component (c) is blended, as necessary, in the first paste, for making the first paste acidic. By making the first paste acidic, the activity of (b) at least one of an aromatic sulfinic acid and a salt thereof improves. Specific examples of (c) an acidic compound include organic acids such as citric acid, succinic acid, oxalic acid, fumaric acid, tartaric acid, malic acid, maleic acid, ethylenediaminetetraacetic acid, polyacrylic acid, and acrylic acid-maleic acid copolymer, inorganic acids such as phosphoric acid, hydrochloric acid, sulfuric acid, and nitric acid, and ester derivatives thereof. They may be used alone, and a mixture of two or more kinds may also be used.

On the other hand, in the second embodiment of the present invention, the first paste certainly includes (a") a (meth)acrylate compound having an acid group(s), which makes the first paste acidic. Therefore, in the second embodiment, the first paste does not necessarily include (c) an acidic compound like in the first embodiment.

The blending amount of (c) an acidic compound in the first embodiment of the present invention is, in the first paste, preferably in the range of from 0.01 mass % to 20 mass %. If the amount is less than 0.01 mass %, it is difficult to improve the activity of (b) at least one of an aromatic sulfinic acid and a salt thereof, and if the amount is more than 20 mass %, the activity of (b) at least one of an aromatic sulfinic acid and a salt thereof may degrade and the preservative property of the paste tends to be worse. More preferably, the amount is in the range of from 0.1 mass % to 10 mass %.

In order to improve the strength of the hardened body of the composition and improve the operability of the paste, it is preferable that at least either one of the first paste and the second paste includes (f) a filler.

As (f) a filler, fillers conventionally blended in dental polymerizable compositions may be used without particular limitations. Examples thereof include powders of: glasses such as silica, barium glass, alumina glass, potassium glass, and fluoroaluminosilicate glass; synthesized zeolite; calcium phosphate; feldspar; fumed silica; aluminum silicate; calcium silicate; magnesium carbonate; hydrous silicate; hydrous calcium silicate; hydrous aluminum silicate; and quarts. In addition, glasses including oxides, sulfides, and fluorides of barium, strontium, yttrium, etc., are used as necessary, for having an X-ray contrasting property.

The surface of the above-described (f) a filler may be treated with a silane coupling agent such as γ-methacryloxypropyltrimethoxysilane, vinyltrichlorosilane, vinyltriethoxysilane, vinyltrimethoxysilane, vinyltriacetoxysilane, and vinyltri(methoxyethoxy)silane. Acetic acids may be added in the silane coupling agent. In acetic acids, anhydrous silicate, hydrous silicate, hydrous calcium silicate, and hydrous aluminum silicate are preferable, because they have the effect of preventing gelling of each component before polymerization, even if the component is stored for a long time.

In addition, an organic-inorganic composite filler produced by pulverizing a hardened body of a mixture of (f) a filler and a (meth)acrylate compound may also be used. These fillers may be used alone, and a mixture of two or more kinds may also be used. It is of course possible to use different fillers for the first paste and the second paste. Fine silicate whose size is in the range of 0.01 μm to 0.1 μm may also be used for adjusting the viscosity of each paste.

When (f) a filler is blended in the first paste, the blending amount is preferably in the range of from 5 mass % to 80 mass % in the first paste. If the amount is less than 5 mass %, the viscosity as a paste tends to be insufficient, and if the amount is more than 80 mass %, the paste gets too hard and the operability tends to degrade. More preferably, the amount is in the range of from 15 mass % to 60 mass %.

The other paste in the two-paste polymerizable composition according to the present invention is referred to as a second paste. The same paste is applied as the second paste of the first embodiment and the second paste of the second embodiment in the present invention. The second paste includes the above-described (a) a (meth)acrylate compound, (d) an organic metal compound, and (e) an organic halogen compound. The second paste may further include (f) a filler in the relationship with the first paste.

The same compound as the compound used in the first paste may be used for (a) a (meth)acrylate compound of the second paste. Of course, a (meth)acrylate compound different from a (meth)acrylate compound of the first paste may be used for the second paste.

The blending amount of (a) a (meth)acrylate compound in the second paste is preferably in the range of from 15 mass % to 95 mass %. If the amount is less than 15 mass %, it is difficult to make a paste, and if the amount is more than 95 mass %, the operability gets worse, and the strength also tends to degrade. More preferably, the amount is in the range of from 40 mass % to 80 mass %.

The polymerization initiators to be blended in the second paste are (d) an organic metal compound and (e) an organic halogen compound. The reaction of them with (b) at least one of an aromatic sulifinic acid and a salt thereof generates radicals.

Examples of the organic metal compound which is the component (d) include copper acetylacetonate, copper 4-cyclohexylbutyrate, copper gluconate, copper acetate, copper oleate, manganese acetylacetonate, manganese naphthenate, manganese octoate, cobalt acetylacetonate, cobalt naphthenate, lithium acetylacetonate, lithium acetate, zinc acetylacetonate, zinc naphthenate, nickel acetylacetonate, nickel acetate, aluminum acetylacetonate, calcium acetylacetonate, chromium acetylacetonate, iron acetylacetonate, sodium naphthenate, and rare earth octoate. They may be used alone, and a mixture of two or more kinds thereof may also be used.

The blending amount of (d) an organic metal compound is preferably in the range of from 0.001 mass % to 1 mass % in the second paste. If the amount is less than 0.001 mass %, the effect is difficult to be obtained, and if the amount is more than 1 mass %, the composition after polymerization tends to discolor. More preferably, the amount is in the range of from 0.005 mass % to 0.1 mass %.

Examples of an organic halogen compound which is the component (e) include benzyltributylammonium chloride, benzyldimethylcetylammonium chloride, benzyldimethylstearylammonium chloride, benzyltriethylammonium bromide, benzyltrimethylammonium chloride, cetalkonium chloride, cetylpyridinium bromide, cetylpyrimidinium chloride, cetyltriethylammonium bromide, didecyldimethylammonium chloride, dilauryldimethylammonium chloride, benzyl lauryldimethylammonium chloride, domiphen bromide, lauryltrimethylammonium chloride, tetra-n-butylammonium bromide, tetra-n-butylammonium chloride, tetra-n-butylammonium iodide, tetradecyltrimethylammonium bromide, tetraethylammonium bromide, tetraethylammonium iodide, trioctylmethylammonium chloride, and dodecyltrimethylammonium chloride. They may be used alone, and a mixture of two or more kinds may also be used.

The blending amount of (e) an organic halogen compound is preferably in the range of from 0.001 mass % to 10 mass % in the second paste. If the amount is less than 0.001 mass %, the effect is difficult to be obtained, and if the amount is more than 10 mass %, the organic halogen compound does not dissolve in the second paste and polymerization reaction is difficult to be obtained. The amount is more preferably in the range of from 0.01 mass % to 1 mass %, and further preferably in the range of from 0.05 mass % to 0.5 mass %.

In order to increase the strength of the hardened body of the composition and to improve the operability of the paste, the second paste may include (f) a filler. For (f) a filler used in the second paste, the same fillers which may be used in the first paste may be used. Of course, a filler different from the filler used in the first paste may be used for the second paste.

When (f) a filler is blended in the second paste, the blending amount thereof is preferably in the range of from 5 mass % to 80 mass % in the second paste. If the amount is less than 5 mass %, the viscosity as a paste tends to be insufficient, and if the amount is more than 80 mass %, the paste gets too hard and the operability tends to degrade. The amount is more preferably in the range of from 15 mass % to 60 mass %.

Next, a third embodiment of the present invention will be described. In the third embodiment, the first paste includes (a) a (meth)acrylate compound, (b) at least one of an aromatic sulfinic acid and a salt thereof, and (c) an acidic compound, and does not include (f) a filler. The second paste includes the above described (a) a (meth)acryate compound, (d) an organic metal compound, and (e) an organic halogen compound, and does not include (f) a filler.

That is, the third embodiment of the present invention is same as the first embodiment except that neither the first paste nor the second past includes (f) a filler. In the first embodiment, at least either one of the first paste and the second includes (f) a filler. Therefore the explanation thereof will be omitted.

The third embodiment of the present invention does not include (f) a filler. Therefore it can be used when a hardened body having a low strength and a hardened body having a low viscosity are desired. In addition, it is also possible to optimize the strength and viscosity by adding a plasticizing agent and the like.

The two-paste polymerizable composition according to the present invention may adequately include a polymerization inhibitor such as dibutylhydroxytoluene, a photopolymerization initiator such as camphaquinone, a peroxide, an anitioxidant, an ultraviolet absorber, a colorant, an antibacterial agent, a fluorescent agent, a flavoring agent, and the like.

In addition, a solvent may be added to the two-paste polymerizable composition according to the present invention, for the purpose of adjusting pH, improving preserving property by the chelate effect of metal ions, and so on. Examples of the solvent include organic solvents such as water and ethanol. The blending amount of the solvent is preferably in the range of from 0 mass % to 80 mass %. If the amount is more than 80 mass %, the amounts of other components get too small and the composition tends not to harden.

On the other hand, other polymerization initiators that do not contribute to the effect of inhibiting oxygen inhibition layers, such as tertiary amines, and pyrimidinetrione derivatives are preferably not blended.

In the two-paste polymerizable composition according to the present invention, the mixing ratio of the first paste and the second paste is, preferably in the range of from 1:10 to 10:1, by mass ratio. If the ratio is out of this range, the operability tends to degrade. The ratio is more preferably in the range of from 1:4 to 4:1.

As long as the above-described action principle to improve the polymerization reaction and preservation stability is satisfied, the two-paste polymerizable composition according to the present invention may include a polymerizable composition that appears to have three or more pastes, by optionally further dividing at least one of the first paste and the second paste into a plurality of pastes.

EXAMPLES

The raw materials were kneaded with the blending amounts shown in Tables 1 and 2, whereby the first and second pastes were produced. With the pastes, the following tests were carried out on the compositions of Examples and Comparative Examples, and the evaluation of the two-paste polymerizable composition according to the present invention was carried out. Mass % was applied to the numerical values in Tables 1 and 2.

Stickiness Evaluation of Hardened

On a glass plate (20 mm×30 mm×1 mm), a rectangular mold (20 mm×20 mm×1 mm) made of a silicone impression material (product name: FUSION, manufactured by GC CORPORATION) was put. A metal ring (inner diameter: 15 mm, height: 1 mm) was put on the mold. After that, for each of Examples and Comparative Examples, the metal ring was filled with the kneaded material obtained by kneading of the first paste and the second paste at the mass ratio of 1:1. Then, a silicone impression material same as the above-described silicone impression material and a glass plate same as the above-described glass plate were put in the order mentioned, and welded by pressure. After 5 minutes were past since the kneading was started, the glass plates and the silicone impression materials were removed. The stickiness of the surface of the hardened body was observed by watching and touching. Every work was carried out at a constant temperature of 23° C. and a constant humidity of 50%. The results are together shown in Tables 1 and 2. The stickiness was evaluated with the scales shown below.

⊚: No stickiness was found
○: A bit of stickiness was found
x: Stickiness was found

TABLE 1

(unit: mass %)

| | | | | Ex. 1 | Ex. 2 | Ex. 3 | Ex. 4 | Ex. 5 | Ex. 6 | Ex. 7 | Ex. 8 |
|---|---|---|---|---|---|---|---|---|---|---|---|
| First paste | (a) (meth)ac-rylate com-pound | (a') (meth)acrylate compound not having acid group | di-2-methacryloxyethyl2,2,4-trimethylhexa-methylenedicarbamate | 56 | 50 | 56 | 45 | 45 | 56 | 45 | 56 |
| | | | triethyleneglycoldimethacrylate ("3G") manufactured by Shin-Nakamura | 14 | 10 | 14 | 10 | 10 | 14 | 10 | 12 |

TABLE 1-continued (unit: mass %)

| | | | Ex. 1 | Ex. 2 | Ex. 3 | Ex. 4 | Ex. 5 | Ex. 6 | Ex. 7 | Ex. 8 |
|---|---|---|---|---|---|---|---|---|---|---|
| | (a'') (meth)acrylate compound having acid group | Chemical Co., Ltd.) 10-methacryloyloxydecyldihydrogenphosphate | | | | | | | | |
| | (b) at least one of aromatic sulfinic acid and salt thereof | sodium benzenesulfinate | 0.4 | 2 | 0.4 | 0.5 | | 0.4 | | 0.4 |
| | | sodium p-toluenesulfinate | | | | | 1 | | 1 | |
| | barbituric acid | 1-cyclohexyl-5-ethylbarbituric acid | | | | | | | | |
| | peroxide | benzoyl peroxide | | | | | | | | |
| | (c) acidic compound | phosphoric acid | 1 | 5 | | 0.5 | 1 | 1 | 0.5 | 1 |
| | | monoisodecylphosphate ("MP-10" manufactured by DAIHACHI CHEMICAL INDUSTRY CO., Ltd.) | | | 2 | | | | | |
| | (f) filler | fumed silica ("RX50" manufactured by NIPPON AEROSIL) | 28.5 | 32.9 | 27.5 | | | 28.5 | | 28.5 |
| | | 7% methacryloyloxypropyl-trimethoxysilane treated silica filler | | | | 43.9 | 42.9 | | 43.4 | |
| | polymerization inhibitor | dibutylhydroxytoluene | 0.1 | 0.1 | 0.1 | 0.1 | 0.1 | 0.1 | 0.1 | 0.1 |
| | solvent | water | | | | | | | | 2 |
| | | ethanol | | | | | | | | |
| Second paste | (a) (meth)acrylate compound | di-2-methacryloxyethyl2,2,4-trimethylhexamethylene-dicarbamate | 45 | 45 | 55 | 45 | 40 | 60 | 60 | 45 |
| | | triethyleneglycoldimethacrylate ("3G" manufactured by Shin-Nakamura Chemical Co., Ltd.) | 15 | 15 | 15 | 10 | 10 | 10 | 10 | 15 |
| | (d) organic metal compound | copper acetylacetonate | 0.01 | 0.01 | 0.02 | 0.01 | 0.01 | | 0.02 | 0.01 |
| | | copper(II) acetate monohydrate | | | | | | 0.01 | | |
| | (e) organic halogen compound | dilauryldimethylammonium chloride | 0.1 | 0.1 | 0.2 | 0.1 | 0.1 | 0.1 | | 0.1 |
| | | dodecyltrimethylammonium chloride | | | | | | | 0.2 | |
| | tertiary amine | p-tolyldiethanolamine | | | | | | | | |
| | (f) filler | fumed silica ("RX50" manufactured by NIPPON AEROSIL) | | | | 29.68 | | 29.79 | 27.88 | |
| | | 7% methacryloyloxypropyl-trimethoxysilane treated silica filler | 39.79 | 39.79 | | 44.79 | 47.99 | | | 39.79 |
| | polymerization inhibitor | p-methoxyphenol | 0.1 | 0.1 | 0.1 | 0.1 | 0.1 | 0.1 | 0.1 | 0.1 |
| | photopolymerization initiator | camphaquinone | | | | | | 0.2 | 0.2 | |
| | | 2,4,6-trimethylbenzoyldi-pheylphosphine oxide | | | | | | 0.1 | 0.1 | |
| | | p-dimethylaminobenzoic acid ethyl | | | | | | 1.5 | 1.5 | |
| | solvent | ethanol | | | | | | | | |
| stickiness evaluation | | | ⊚ | ⊚ | ⊚ | ⊚ | ⊚ | ⊚ | ⊚ | ⊚ |

TABLE 2

(unit: mass %)

| | | | | Ex. 9 | Ex. 10 | Ex. 11 | Ex. 12 | Comp. Ex. 1 | Comp. Ex. 2 | Comp. Ex. 3 |
|---|---|---|---|---|---|---|---|---|---|---|
| First paste | (a) (meth)acrylate compound | (a') (meth)acrylate compound not having acid group | di-2-methacryloxyethyl2,2,4-trimethylhexamethylenedicarbamate | 53 | 33 | 79 | 79 | 56 | 52 | 40 |
| | | | triethyleneglycoldimethacrylate ("3G") manufactured by Shin-Nakamura Chemical Co., Ltd. | 13 | 13 | 19.9 | 19.9 | 14 | 18 | 15 |
| | | (a'') (meth)acrylate compound having acid group | 10-methacryloyloxydecyldihydrogenphosphate | | 5 | | | | | |
| | (b) at least one of aromatic sulfinic acid and salt thereof | | sodium benzenesulfinate | 0.5 | 2 | 0.5 | 0.5 | 0.4 | | 0.4 |
| | | | sodium p-toluenesulfinate | | | | | | | |
| | barbituric acid | | 1-cyclohexyl-5-ethylbarbituric acid | | | | | | 1 | |
| | peroxide | | benzoyl peroxide | | | | | | | 0.5 |

TABLE 2-continued (unit: mass %)

| | | | Ex. 9 | Ex. 10 | Ex. 11 | Ex. 12 | Comp. Ex. 1 | Comp. Ex. 2 | Comp. Ex. 3 |
|---|---|---|---|---|---|---|---|---|---|
| | (c) acidic compound | phosphoric acid monoisodecylphosphate ("MP-10" manufactured by DAIHACHI CHEMICAL INDUSTRY CO., Ltd.) | | | 1 | 0.5 | 0.5 | | |
| | (f) filler | fumed silica ("RX50" manufactured by NIPPON AEROSIL) | 28.4 | 30.9 | | | | 29.5 | 28.9 |
| | | 7% methacryloyloxypropyl-trimethoxysilane treated silica filler | | | | | | | | 44 |
| | polymerization inhibitor | dibutylhydroxytoluene | 0.1 | 0.1 | 0.1 | 0.1 | 0.1 | 0.1 | 0.1 |
| | solvent | water | | | | | | | |
| | | ethanol | | 20 | | | | | |
| Second paste | (a) (meth)acrylate compound | di-2-methacryloxyethyl2,2,4-trimethylhexamethylenedicarbamate | 60 | 34 | 79.57 | 55 | 45 | 45 | 55 |
| | | triethyleneglycoldimethacrylate ("3G" manufactured by Shin-Nakamura Chemical Co., Ltd.) | 10 | 13 | 20 | 15 | 15 | 15 | 15 |
| | (d) organic metal compound | copper acetylacetonate | | | 0.03 | 0.02 | | | |
| | | copper(II) acetate monohydrate | 0.01 | 0.01 | | | 0.01 | 0.01 | |
| | (e) organic halogen compound | dilauryldimethylammonium chloride | 0.1 | 0.1 | 0.3 | 0.2 | 0.1 | 0.1 | |
| | | dodecyltrimethylammonium chloride | | | | | | | |
| | tertiary amine | p-tolyldiethanolamine | | | | | | | 0.5 |
| | (f) filler | fumed silica ("RX50" manufactured by NIPPON AEROSIL) | 29.79 | 32.79 | | | | | 29.4 |
| | | 7% methacryloyloxypropyl-trimethoxysilane treated silica filler | | | | 29.68 | 39.79 | 39.79 | |
| | polymerization inhibitor | p-methoxyphenol | 0.1 | 0.1 | 0.1 | 0.1 | 0.1 | 0.1 | 0.1 |
| | photopolymerization initiator | camphaquinone 2,4,6-trimethylbenzoyldi-phenylphosphine oxide p-dimethylaminobenzoic acid ethyl | | | | | | | |
| | solvent | ethanol | | 20 | | | | | |
| stickiness evaluation | | | ⊚ | ○ | ⊚ | ⊚ | X | X | X |

From the results shown in Tables 1 and 2, the two-paste polymerizable compositions according to Examples had less oxygen inhibition layers compared to the compositions of the Comparative Examples.

The invention claimed is:

1. A two-paste polymerizable composition comprising:
a first paste including
   (a) a (meth)acrylate compound,
   (b) at least one of an aromatic sulfinic acid and a salt thereof, and
   (c) an acidic compound; and
a second paste including
   (a) a (meth)acrylate compound,
   (d) an organic metal compound, and
   (e) an organic halogen compound,
wherein at least either one of the first paste and the second paste includes (f) a filler.

2. The two-paste polymerizable composition according to claim 1, comprising:
the first paste including
   (a) a (meth)acrylate compound: in the range of from 15 mass % to 95 mass %,
   (b) at least one of an aromatic sulfinic acid and a salt thereof: in the range of from 0.01 mass % to 5 mass %,
   (c) an acidic compound: in the range of from 0.01 mass % to 20 mass %, and
   (f) a filler: in the range of from 5 mass % to 80 mass %; and
the second paste including
   (a) a (meth)acrylate compound: in the range of from 15 mass % to 95 mass %,
   (d) an organic metal compound: in the range of from 0.001 mass % to 1 mass %,
   (e) an organic halogen compound: in the range of from 0.001 mass % to 10 mass %, and
   (f) a filler: in the range of from 5 mass % to 80 mass %.

3. A two-paste polymerizable composition comprising:
a first paste including
   (a') a (meth)acrylate compound not having acid groups,
   (a") a (meth)acrylate compound having an acid group(s), and
   (b) at least one of an aromatic sulfinic acid and a salt thereof; and
a second paste including
   (a) a (meth)acrylate compound,
   (d) an organic metal compound, and
   (e) an organic halogen compound,
wherein at least either one of the first paste and the second paste includes (f) a filler.

4. The two-paste polymerizable composition according to claim 3, comprising:
the first paste including
   (a') a (meth)acrylate compound not having acid groups and (a") a (meth)acrylate compound having an acid group(s), whose total amount is: in the range of from 15 mass % to 95 mass %,
- (b) at least one of an aromatic sulfinic acid and a salt thereof: in the range of from 0.01 mass % to 5 mass %, and
- (f) a filler: in the range of from 5 mass % to 80 mass %; and the second paste including
- (a) a (meth)acrylate compound: in the range of from 15 mass % to 95 mass %,
- (d) an organic metal compound: in the range of from 0.001 mass % to 1 mass %,
- (e) an organic halogen compound: in the range of from 0.001 mass % to 10 mass %, and
- (f) a filler: in the range of from 5 mass % to 80 mass %.

5. A two-paste polymerizable composition comprising:

a first paste including
- (a) a (meth)acrylate compound,
- (b) at least one of an aromatic sulfinic acid and a salt thereof, and
- (c) an acidic compound; and a second paste including
- (a) a (meth)acrylate compound,
- (d) an organic metal compound, and
- (e) an organic halogen compound, wherein neither the first paste nor the second paste includes (f) a filler.

* * * * *